United States Patent [19]

Sekiguchi et al.

[11] 4,248,793

[45] Feb. 3, 1981

[54] PROCESS FOR THE PRODUCTION OF INTERNAL OLEFIN SULFONATE

[75] Inventors: Shizuo Sekiguchi, Funabashi; Katsumasa Nagano, Ichikawa; Yozo Miyawaki, Funabashi; Kyozo Kitano, Chiba, all of Japan

[73] Assignee: The Lion Fat & Oil Co., Ltd., Tokyo, Japan

[21] Appl. No.: 79,139

[22] Filed: Sep. 26, 1979

[51] Int. Cl.³ .................................................. C07C 143/16
[52] U.S. Cl. .................................................. 260/513 T
[58] Field of Search ........................ 260/513 T, 504 S

[56] References Cited

U.S. PATENT DOCUMENTS

| | | | |
|---|---|---|---|
| 2,530,757 | 11/1950 | Bransky et al. | 260/504 S |
| 3,444,087 | 5/1969 | Eccles et al. | 260/513 T |
| 3,444,191 | 5/1969 | Nielsen | 260/513 T |

Primary Examiner—Alan Siegel
Attorney, Agent, or Firm—Blanchard, Flynn, Thiel, Boutell & Tanis

[57] ABSTRACT

Process for the production of light-colored internal olefin sulfonates substantially free from unreacted olefins comprises sulfonating an internal olefin with gaseous $SO_3$ to produce a sulfonation reaction mixture, neutralizing said sulfonation reaction mixture with caustic alkali without hydrolysis of sulton contained in the mixture, adding to the neutralized sulfonation reaction mixture an extracting reagent selected from halogenated hydrocarbons to form an extract phase containing unreacted olefin and a raffinate phase containing internal olefin sulfonates and sultons, and hydrolyzing the resulting raffinate phase in the presence of caustic alkali.

4 Claims, No Drawings

PROCESS FOR THE PRODUCTION OF INTERNAL OLEFIN SULFONATE

BACKGROUND OF THE INVENTION

The present invention relates to a process for producing internal olefin sulfonates, being light-colored and substantially free from unreacted olefins, from a straight-chain internal olefin having from 10 to 22 carbon atoms.

It is well known that an olefin sulfonate, which can be used as an active component for detergents and the like, is obtainable through the steps of sulfonating an olefin with gaseous $SO_3$, neutralizing the resulting sulfonation product, and thereafter hydrolyzing the same. In this case, as the starting material olefin there is commonly utilized vinylidene type olefin or alpha olefin, but an internal olefin is scarcely utilized therefor. In particular, this is because the internal olefin, which has a low reactivity to gaseous $SO_3$ as compared with vinylidene type olefin or alpha olefin, can produce only a sulfonation product being deteriorated in color tone and moreover containing a large quantity of unreacted olefin under the conventional sulfonation conditions. As a matter of course, the quantity of unreacted olefin contained in the sulfonation product can be reduced to a certain extent by employing relatively severe sulfonation conditions, but in this case the sulfonation product is colored more conspicuously.

SUMMARY OF THE INVENTION

An object of this invention is to provide a process for producing olefin sulfonates being light-colored and substantially free from unreacted olefin by using, as a starting material, a straight-chain internal olefin having from 10 to 22 carbon atoms, being characterized in that a starting olefin is sulfonated under relatively mild conditions to thereby prevent a sulfonation product from being colored and an unreacted olefin mingled with the sulfonation product is separated by the aid of solvent extraction and recovered after neutralization of and after hydrolysis of the sulfonation product.

Accordingly, the present invention provides a process for producing internal olefin sulfonates which comprises: (a) sulfonating an internal olefin having from 10 to 22 carbon atoms with gaseous $SO_3$, at a molar ratio of less than 1 mole of $SO_3$ per 1 mole of said internal olefin, under conditions effective to produce a sulfonation reaction mixture which contains at least 20% by weight of unreacted internal olefin; (b) neutralizing said sulfonation reaction mixture with caustic alkali at a temperature of 10 to 80° C.; (c) commingling the neutralized sulfonation reaction mixture with an extracting reagent selected from halogenated hydrocarbons having a specific gravity of 1.2 or more, in a weight ratio of said neutralized mixture to the extracting reagent of from 0.1 to 5, to form a raffinate phase containing internal olefin sulfonates and sultones and an extract phase containing unreacted internal olefin dissolved therein; and (d) hydrolyzing said raffinate phase in the presence of caustic alkali at a temperature of 110° to 180° C.

DETAILED DESCRIPTION OF THE INVENTION

The starting internal olefin which may be used in the present invention includes olefins such as octadecene having a double bond at the 2-9 position, hexadecene having a double bond at the 2-8 position, tetradecene having a double bond at the 2-7 position, etc. The starting internal olefin employed in the present invention may contain alpha olefins having from 10 to 22 carbon atoms in an amount of up to 50% by weight.

As the conditions for sulfonating the starting internal olefin there can be employed substantially the same sulfonation conditions as are employed for vinylidene type olefins or alpha olefins with the exception that the molar ratio of the gaseous $SO_3$ to the starting olefin is low, that is, less than 1. Meantime, the highly reactive vinylidene type olefins or α-olefins are usually sulfonated under the conditions including $SO_3$/olefin molar ratio of 1 or more, temperature of 60° C. or less, and residence time of about 15 seconds. Generally speaking, the rate of sulfonation reaction is dependent largely upon the $SO_3$/olefin molar ratio rather than the reaction temperature and residence time. Therefore, in so far as the $SO_3$/olefin molar ratio is maintained to be less than 1, preferably 0.89–0.95, the coloration caused by the sulfonation may be suppressed within the maximum permissible limit. However, when the reaction temperature and/or residence time are extremely increased, even if the $SO_3$/olefin molar ratio is maintained within the above-mentioned range, it is unavoidable that the coloration of the sulfonation product is increased. In the case of the present invention, on the other hand, the indirect control of the sulfonation conditions can be effected by controlling the quantity of unreacted olefin contained in the sulfonation reaction mixture being produced.

The sulfonation process according to the present invention may be carried out by employing either of the thin film type sulfonation system and stirred tank type sulfonation system. And the sulfonating agent, i.e., gaseous $SO_3$ normally enters the system in such a state that $SO_3$ is diluted with inert gases at a concentration of 1 to 20% by volume.

The sulfonation reaction mixture resulting from the sulfonation step of the present invention is subjected to the neutralization. Taking the unreacted olefin out of consideration, the mixture is comprised predominantly of alkene sulfonic acids and sultones and contains small quantities of disulfonated products and impurities. The neutralization step of the present invention is exclusively directed toward the neutralization alkene sulfonic acid and therefore it is preferred to avoid hydrolysis of sultones in this step. This is because when the hydrolysis of sultones takes place in this neutralization step, solvent extraction of the unreacted olefin is thereby next to impossible. As neutralizing agents there can be employed caustic alkalis such as caustic soda, caustic potash and the like. The quantity of caustic alkali used in the neutralization step is sufficient to be capable of neutralizing the alkene sulfonic acid contained in the sulfonation reaction mixture resulting from the sulfonation step, but it is operationally desirable to add the caustic alkali required for hydrolysis of sultones previously in the neutralization step. The neutralization reaction is carried out at a temperature of 10° to 80° C., but in so far as this temperature range is observed, sultone is not hydrolyzed for practical purposes.

The neutralized mixture resulting from the neutralization step is subjected to solvent extraction. As the extracting reagent there may be employed halogenated lower hydrocarbons having a specific gravity of 1.2 or more which possess a strong solubility to the unreacted olefins and on the other hand, a weak solubility to water. The aforesaid halogenated lower hydrocarbons include carbon tetrachloride, trichloroethylene, tribromomethane, ethylene dibromide, acetylene dibromide, etc. The quantity of extracting reagent used is preferred to be in the range where the weight ratio of the neutralized mixture to extracting reagent is 0.1 to 5. When the mixing of the neutralized mixture with extracting reagent is effected within this range there can be formed, due to the difference in specific gravity of ingredients, a raffinate phase, which contains a sultones-containing olefin sulfonate, in the upper layer and an extract phase, which contains an unreacted olefin-containing extracting reagent, in the lower layer.

As is evident from the above-mentioned, the solvent extraction employed in the present invention may be said to be one wherein the unreacted olefin is selectively extracted by making use of the differences in solubility to the extracting reagent. Therefore, it is necessary for the co-existing alkene sulfonate to be neutralized so as to assume a salt form, but it is not necessarily required to carry out the neutralization and solvent extraction separately and successively.

In the case of the present invention, from the operational viewpoint it is rather desirable to carry out both neutralization and solvent extraction at a single stroke. In this case, predetermined quantities of caustic alkali and extracting reagent are commingled with the sulfonation reaction mixture, thereby permitting settled separation of the raffinate phase containing sulfonate and sultone in the upper layer and the extract phase containing unreacted olefin in the lower layer.

The raffinate and extract phases are separated from each other, for instance, by means of a separating funnel, decantation, etc. The thus separated raffinate phase is heated to a temperature of 110° to 180° C., whereby the sultone present in the raffinate phase is hydrolyzed so as to become olefin sulfonate. The caustic alkali required for the hydrolysis of sultone may be added to the raffinate phase at the time of heating, but when an excessive quantity of caustic alkali has been used in the preceeding neutralization step as mentioned above it avoids the necessity of newly adding the caustic alkali at the heating stage.

On the other hand, the extract phase separated from the raffinate phase contains a little quantity of moisture, but when it is subjected to distillation after dehydration, the extracting reagent and unreacted olefin can thus be recovered, whereby the former may be re-used as part of the extracting reagent of the present invention and the latter may be re-used as part of the starting olefin respectively.

As above-mentioned, the present invention, while employing the internal olefin having a low reactivity as the starting material, makes it possible to prevent the conspicuous coloration of the sulfonation product by prescribing the relatively mild sulfonation conditions and additionally to remove the unreacted olefin increased due to the employment of said relatively mild sulfonation conditions almost completely from the final product by means of solvent extraction. According to the present invention, accordingly, it is made possible to produce internal olefin sulfonates being superior in color tone and substantially free from the unreacted olefin.

EXAMPLE

Four varieties of tests were carried out for sulfonating internal olefins of different carbon numbers while changing the sulfonation conditions by the use of a glass-made thin film type sulfonation means with an inside diameter of 6 mm and a length of 1.0 m, wherein $SO_3$ was employed in each test whose concentration had been diluted to 2 volume % with nitrogen.

A part of the sulfonation reaction mixture obtained according to each test was diluted with a 99% ethanol aqueous solution at a concentration of 5%. And color tone $[(-\log T) \times 10^3]$ was measured on the respective thus diluted sulfonation reaction mixtures by means of an absorption photometer manufactured by HITACHI LTD. under the conditions: wavelength 420m$\mu$ and slit width 0.05 mm. Each 10 g of the undiluted sulfonation reaction mixture was accurately metered and placed in a 2 l round-bottomed flask (equipped with a reflux condenser and a water measuring tube). To the same were added 300 ml of ethylene glycol and 300 ml of a 48% NaOH aqueous solution. This was subjected to azeotropic distillation at a liquid temperature of 190° C. for about 20 minutes to thereby distill the unreacted olefin out. And the quantity of the unreacted olefin (represented by F-OIL (%) ) contained in the sulfonation reaction mixture was measured based on the quantity thus distilled out in each test.

In Table-1 are shown the carbon number of the starting internal olefin used in each test, sulfonation conditions, color tone of the sulfonation reaction mixture and the quantity of the unreacted olefin respectively.

Table-1

| Test No. | Carbon number of internal olefin | Sulfonation conditions | | Sulfonation reaction mixture | |
|---|---|---|---|---|---|
| | | $SO_3$ molar ratio | Temperature | Color tone | F-OIL (%) |
| 1 | $C_{11}-C_{14}$ | 0.95 | 20 | 300 | 37.4 |
| 2 | $C_{14}$ | 0.95 | 20 | 240 | 41.5 |
| 3 | $C_{16}-C_{18}$ | 0.9 | 50 | 140 | 40 |
| 4 | $C_{16}-C_{18}$ | 1.5 | 50 | 2900 | 8.3 |

The results shown in Table-1 indicate that the employment of severe sulfonation conditions serves to decrease the quantities of unreacted olefins contained in the sulfonation reaction mixture, while the color tone is deteriorated conspicuously.

Next, to 100 g of the sulfonation reaction mixture obtained from Test No. 1 were added 300 g of ethylene dibromide and further 200 g of a 5% NaOH aqueous solution and mixed. This mixture was stirred at a temperature of 40° C. for about 5 minutes to thereby neutralize the olefin sulfonate contained in the sulfonation reaction mixture. After completion of stirring, the above mixture was left standing for about 5 minutes so that a raffinate phase might be formed in the upper layer and an extracted extract phase containing unreacted olefin in the lower layer. The raffinate phase was separated from the extract phase by decantation, and 263 g of this raffinate phase was stirred at a temperature of 140° C. for 30 minutes in an autoclave, whereby the sultone contained in the raffinate phase was hydrolyzed.

Next, a part of the obtained hydrolysis product was diluted with water at a concentration of 5%, and color tone was measured thereon under the conditions: wavelength 420 m$\mu$ and slit width 0.05 mm by means of said absorption photometer. And the unreacted olefin contained in the hydrolysis product was extracted with petroleum ether, and the quantity of the unreacted olefin being residual in the hydrolysis product was calculated in terms of % by weight against the sodium olefin sulfonate.

Likewise, 100 g of each of the sulfonation reaction mixtures obtained from Test No. 2 and No. 3 was treated in the same manner while changing the kind and quantity of the extracting reagent used, thereby measuring the color tone of the hydrolysis product and the quantity of the unreacted olefin respectively. The results thus obtained are as shown in Table-2.

For comparison purposes, furthermore, 100 g of each of the sulfonation reaction mixtures obtained from Test Nos. 1-4 was added with 200 g of a 5% NaOH aqueous solution and was stirred, without addition of an extracting reagent, at 40° C. for 10 minutes, followed by additional 30 minutes' stirring at 140° C., thereby neutralizing the sulfonic acid and hydrolyzing the sultone, which are contained in the mixture. The color tone and the quantity of the unreacted olefin were measured on the thus obtained hydrolysis product in the same manner as the preceding instance. The obtained results are as shown in Table-2. In this respect, extraction of the unreacted olefin contained in the hydrolysis product obtained from the sulfonation reaction mixture of Test No. 3 was tried in the manner of adding 300 g of ethylene bromide to 300 g of the hydrolysis product, but the mixture revealed an emulsion state, thereby rendering the intended extraction impossible.

For comparison purposes, still further, 200 g of 0.5% NaOH aqueous solution and 300 g of normal hexane were added to 100 g of the sulfonation reaction mixture obtained from Test No. 3 and mixed. The mixture was stirred at 40° C. for 10 minutes, and thereafter was left standing for 60 minutes. As a result of this standing, the mixture was separated into two layers, the upper layer of which comprises the normal hexane and the sulfonation product and the lower layer of which was a NaOH aqueous solution. In other words, the use of normal hexane as the extracting reagent rendered impossible either the neutralization of the sulfonation product or the extraction of the unreacted olefin.

obtained a hydrolysis product (olefin sulfonate) which contains little unreacted olefin and is superior in color tone. In contrast, in the cases of Tests k-m, wherein the internal olefins are sulfonated under relatively mild conditions but no solvent extraction is effected, a large quantity of unreacted olefin is contained in the resulting hydrolysis product, while in the case of Test n, wherein the severe sulfonation conditions are employed, the unreacted olefin is little but on the other hand the color tone is inferior exceedingly.

We claim:
1. A process for producing internal olefin sulfonates which comprises:
 (a) sulfonating an internal olefin having from 10 to 22 carbon atoms with gaseous $SO_3$, at a molar ratio of less than 1 mole of $SO_3$ per 1 mole of said internal olefin, under conditions effective to produce a sulfonation reaction mixture which contains at least 20% by weight of unreacted internal olefin;
 (b) neutralizing said sulfonation reaction mixture with caustic alkali at a temperature of 10° to 80° C.;
 (c) commingling the neutralized sulfonation reaction mixture with an extracting reagent selected from halogenated hydrocarbons having a specific gravity of 1.2 or more, in a weight ratio of said neutralized mixture to the extracting reagent of from 0.1 to 5, to form a raffinate phase containing internal olefin sulfonates and sultones and an extract phase containing unreacted internal olefin dissolved therein; and
 (d) hydrolyzing said raffinate phase in the presence of caustic alkali at a temperature of 110° to 180° C.

2. A process according to claim 1, wherein the extracting reagent is selected from the group consisting of carbon tetrachloride, trichloroethylene, tribromomethane, ethylene dibromide and acetylene dibromide.

3. A process according to claim 1, wherein the starting internal olefin contains up to 50% by weight of an alpha olefin having 10 to 22 carbon atoms.

4. A process according to claim 1, wherein steps (b) and (c) are performed at a stroke by adding caustic alkali and the extracting reagent to the sulfonation reaction mixture from step (a).

Table-2

| Test | Sulfonation reaction mixture to be tested | Extraction conditions | | | Hydrolysis product | |
|---|---|---|---|---|---|---|
| | | Name of extracting reagent | Specific gravity | Quantity added (vs. sulfonation product) | Color tone | F-OIL (%) |
| a | Test No. 1 | Ethylene dibromide | 2.17 | 300 | 320 | 3.1 |
| b | Test No. 2 | " | | 300 | 225 | 1.1 |
| c | Test No. 3 | " | | 50 | 130 | 16.0 |
| d | Test No. 3 | " | | 100 | 140 | 8.0 |
| e | Test No. 3 | " | | 200 | 135 | 5.0 |
| f | Test No. 3 | " | | 300 | 145 | 1.0 |
| g | Test No. 3 | Carbon tetrachloride | 1.60 | 300 | 140 | 1.0 |
| h | Test No. 3 | Trichloroethylene | 1.47 | 300 | 125 | 3.1 |
| i | Test No. 3 | Methane tribromide | 2.89 | 300 | 175 | 8.1 |
| j | Test No. 3 | Acetylene dibromide | 2.96 | 300 | 200 | 5.1 |
| k | Test No. 1 | — | — | — | 300 | 36.7 |
| l | Test No. 2 | — | — | — | 220 | 40.5 |
| m | Test No. 3 | — | — | — | 145 | 38.7 |
| n | Test No. 4 | — | — | — | 3050 | 8.3 |

As is evident from the above table, when the internal olefin is sulfonated in accordance with the process of the present invention and the resulting sulfonation reaction mixture is treated in accordance with the process of the present invention (refer to Tests a-j), there can be